(12) United States Patent
Hünig

(10) Patent No.: US 7,868,143 B2
(45) Date of Patent: Jan. 11, 2011

(54) MICROPARTICLE WITH CD28-SPECIFIC MONOCLONAL ANTIBODIES

(75) Inventor: Thomas Hünig, Winterhausen (DE)

(73) Assignee: TheraMAB LLC (RU)

( * ) Notice: Subject to any disclaimer, the term of this patent is extended or adjusted under 35 U.S.C. 154(b) by 116 days.

(21) Appl. No.: 10/520,474

(22) PCT Filed: May 30, 2003

(86) PCT No.: PCT/DE03/01825

§ 371 (c)(1),
(2), (4) Date: Dec. 5, 2005

(87) PCT Pub. No.: WO2004/004768

PCT Pub. Date: Jan. 15, 2004

(65) Prior Publication Data

US 2006/0121021 A1 Jun. 8, 2006

(30) Foreign Application Priority Data

Jul. 4, 2002 (DE) .................... 102 30 223

(51) Int. Cl.
*C07K 16/00* (2006.01)
(52) U.S. Cl. .................. 530/391.1
(58) Field of Classification Search ........ None
See application file for complete search history.

(56) References Cited

U.S. PATENT DOCUMENTS 6,987,171 B1 * 1/2006 Hunig ............ 530/388.75

2002/0058019 A1 5/2002 Berenson et al. .......... 424/93.7

FOREIGN PATENT DOCUMENTS

DE 100 50 935 A1 5/2002
WO WO 98/54225 * 12/1998

OTHER PUBLICATIONS

Huang Z., Pharmacology and Therapeutics, 2000, 86: 201-215.*
Bonhyadi, M. et al., "Xcellerate: An Autologous T Cell Immunotherapy Approach for Treating B-Cell Lymphocyticleukemia (B-CLL)," *Blood*, Nov. 16, 2000, Abstract only, 1 page.
Broeren, Chris P. et al., "Costimulation Light: Activation of CD4+ T Cells with CD80 or CD86 Rather Than Anti-DC28 Leads to a TH2 Cytokine Profile," *The Journal of Immunology*, 2000, 165: 6908-6914.
Mengozzi, Manuela et al., "Naïve CD4 cells inhibit CD28-costimulated R5 HIV replication in memory CD4 T cells," *PNAS*, Sep. 25, 2001, vol. 98, No. 20, pp. 11644-11649.
Dynabeads® M-450 Tosylactivated, Dynal® Biotech, pp. 1-8, date unknown, but prior to the filing date of the instant application, (Jul. 4, 2002).
"Are you new to the Dynabeads® Technology?," http://www.dynal.no/kunder/dynal/dynalpub401.nsf/print/9F9F14DDD7BF78E6C125..., downloaded Jul. 21, 2003, 2 pages.

* cited by examiner

*Primary Examiner*—Ilia Ouspenski
(74) *Attorney, Agent, or Firm*—Mayer & Williams PC

(57) ABSTRACT

The invention relates to microparticles with a support structure and CD28-specific superagonistic monoclonal antibodies (mAbs) bonded to the support structure or a compound mimicking the above.

5 Claims, 14 Drawing Sheets

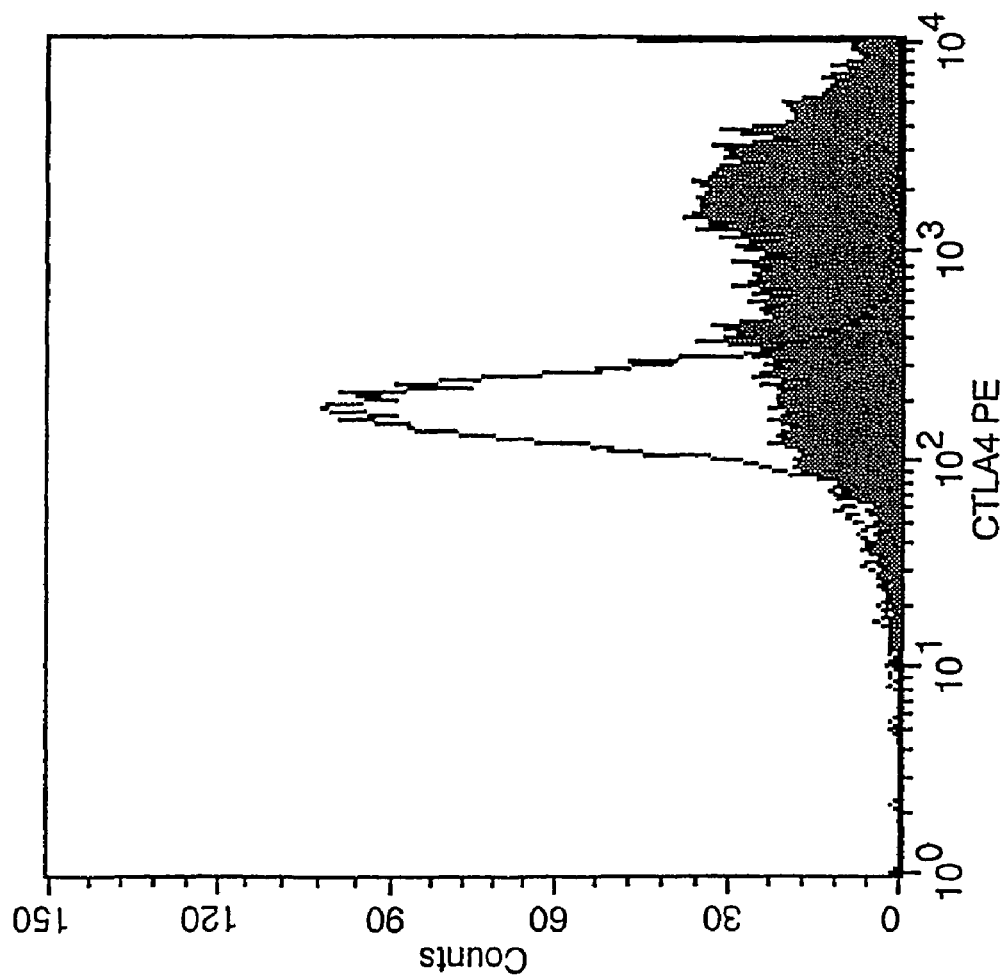

MICROPARTICLE WITH CD28-SPECIFIC MONOCLONAL ANTIBODIES

FIELD OF THE INVENTION

The invention relates to microparticles with a support structure and monoclonal antibodies (mAbs) bonded to the support structure, to the uses of such antibodies and to a method for preparing such microparticles.

BACKGROUND OF THE INVENTION AND PRIOR ART

There exist various diseases for warm-blooded organisms, human or animal, wherein the number of different-type blood cells is reduced or insufficiently active compared to the healthy state.

A first such group of diseases is a pathologically reduced T cell count, in particular CD4 T cell count commonly, such as for AIDS or leukemic diseases in the course of chemotherapy or radiation therapy.

A second group of diseases, where the number or the activity of a certain sub-group of T cells maintaining the immunological tolerance for a healthy person, is reduced or has a disturbed function, comprises autoimmune-inflammatory diseases. Examples are rheumatic arthritis, inflammatory intestinal diseases, diabetes requiring insulin treatment, multiple sclerosis and the Guillain-Barré syndrome.

A third group of diseases is called granulocytopenia (e.g. neutropenia) or monocytopenia and relates to the granulocytes. Reasons for this disease may be: i) reduced granulocytopoiesis or monocytopoiesis (aplastic disturbance) because of bone marrow damages, for instance by chemical substances such as benzene, drugs such as cytostatics, immune suppressants, AZT and/or chloramphenicol (dose-dependent, toxic) or phenylbutazone, gold compounds, rarely chloramphenicol (dose-independent by pharmakinetic reactions), radiation or autoantibodies against stem cells (in some cases of immune neutropenia), because of bone marrow infiltration (leukemias, carcinomas, malignant lymphomas) and/or because of osteomyelosclerosis, ii) maturation disturbances of the granulocytopoiesis, for instance by congenital maturation disturbances of the myelopoiesis, Kostmann's syndrome (maturation stop of the myelopoiesis in the stage of the promyelocytes), cyclic neutropenia, myelodysplasia syndrome, vitamin B12 or folic acid deficiency with ineffective granulo-, erythro- and/or thrombopoiesis. Usual therapies comprise the administration of growth factors of the granulocytopoiesis (for instance G-CSF and GM-CSF).

A fourth group is called thrombocytopenia. Reasons may be: i) reduced thrombocytopoiesis in the bone marrow (aplastic disturbance or reduced megakaryocyte count in the bone marrow) because of bone marrow damages, for instance by chemical substances such as benzene, drugs such as cytostatics and/or immune suppressants, radiation or infections such as HIV, or autoantibodies against megakaryocytes (in some cases of immune thrombocytopenia), because of bone marrow infiltration (leukemias, carcinomas, malignant lymphomas) and/or because of osteomyelosclerosis, ii) maturation disturbances of the megakaryocytes (megakaryocytes in the bone marrow normal or increased) with ineffective thrombo-, erythro- and/or granulopoiesis with megaloblasts, giant rods etc. because of vitamin B12 or folic acid deficiency. Usual therapies comprise the omission of suspicious-appearing drugs, thrombocyte substitution (in case of disturbance of generation in the bone marrow: thrombopoietin) and MGDF (stimulation of the proliferation and maturation of megakaryocytes).

The fifth group are the aplastic anemias or bone marrow failure with aplasia/hypoplasia of the bone marrow and pancytopenia (stem cell disease). A congenital aplastic anemia is for instance the Fanconi's anemia. More frequent are the acquired aplastic anemias, such as the idiopathic aplastic anemia (reason unknown) and secondary aplastic anemias by drugs, toxic substances, ionizing radiation and virus infections (see above). Supportive therapy approaches comprise the substitution of erythrocytes/thrombocytes. Causal therapy approaches comprise the bone marrow transplantation or stem cell transplantation, immunosuppressive therapies (e.g. ATG) and other therapy measures such as administration of cytokines (GM-CSF, G-CSF, MGDF, and/or thrombopoietin).

Finally, in the course of the acute leukemia, there is often anemia, thrombocytopenia and/or granulocytopenia. Therapies comprise the substitution of erythrocytes and thrombocytes as required or the excitation of granulopoiesis by G-CSF and/or GM-CSF, the chemotherapy and bone marrow and/or stem cell transplantation.

It is common to the above diseases of the first and second groups that the respective blood cells carry CD28 on their surfaces. It is common to the third to sixth groups that the concerned blood cells in contrast do not carry CD28 on their surfaces.

For a better understanding of the invention, further the following technological background is important. The activation of resting T cells for the proliferation and functional differentiation requires firstly the occupation of two surface structures, so-called receptors: 1. of the antigen receptor having a different specificity from cell to cell and being necessary for the recognition of antigens, e.g. viral fission products; and of the CD28 molecule equally expressed on all resting T cells with the exception of a sub-group of the CD28 T cells of man, this molecule naturally binding to ligands on the surface of other cells of the immune system. This is the costimulation of the antigen-specific immune reaction by CD28. In a cell culture, these processes can be imitated by occupation of the antigen receptor and of the CD28 molecule with suitable mAbs. In the classic system of the costimulation, neither the occupation of the antigen receptor nor that of the CD28 molecule alone will lead to the T cell proliferation, the occupation of both receptors is however effective. This observation was made for T cells of man, mouse and rat.

There are however also known CD28-specific mAbs, which alone can induce the T cell proliferation. Such a superagonistic activation, i.e. independent from the occupation of the antigen receptor, of resting T lymphocytes by CD28-specific mAbs was found in the following systems: in the document Brinkmann et al., J. Immunology, 1996, 156: 4100-4106, it has been shown that a very small portion (5%) of human T lymphocytes, which because of the missing surface marker CD45 RO could be assigned to the group of the resting T lymphocytes, is activated by the CD28-specific mAb 9.3 normally requiring costimulation when adding the growth factor interleukin-2 (IL-2) without occupation of the antigen receptor. In the document Siefken et al., Cellular Immunology, 1997, 176: 59-65, it has been shown that a CD28-specific mAb prepared in a conventional way, i.e. by immunization of mice with human T cells, can activate in a cell culture a subgroup of human T cells without occupation of the antigen receptor for the proliferation, if CD28 is occupied by this mAb and the cell-bound mAbs are additionally crosslinked with each other by further antibodies. It is common to the in so far known antibodies that only a small portion of the T cells can be activated.

In the document Tacke et al., Eur. J. Immunol., 1997, 27: 239-247, two kinds of CD28-specific monoclonal antibodies with different functional properties have been described; costimulatory mAbs, which costimulate the activation of resting T cells with simultaneous occupation of the antigen receptor only; and superagonistic mAbs, which can activate without occupation of the antigen receptor T lymphocytes of all classes in vitro and in the test animal for proliferation. Both in so far known mAbs originate from an immunization with cells, on which rat CD28 is expressed, and are obtainable by different selections directed toward their respectively described properties. Finally, from the document WO 98/54225, another human CD28-specific superagonistic mAb is known in the art, namely CMY-2.

Surprisingly however, according to the document DE-100 50 935 A1, blood cells not carrying CD28 can also be stimulated with superagonistic CD28-specific mAbs with in vivo applications.

The in so far known superagonistic mAbs meet all requirements with regard to their stimulatory effects, it would however be desirable to need less mAbs for a defined stimulatory effect. Furthermore, the stimulation of T lymphocytes by superagonistic CD28-specific mAbs is up to now limited to two systems each having drawbacks: isolated T lymphocytes can often be stimulated in a cell culture by such mAbs only, if the culture dishes have before been coated with antibodies reacting with the used superagonistic mAbs and secondarily crosslinking. When using unseparated preparations of peripheral blood cells also containing T lymphocytes, and with in vivo application, the superagonistic mAbs may also be used as a soluble substance; the reason for this is presumably that the secondary crosslinking takes place by so-called Fc receptors on the non-T lymphocytes reacting with the constant portion of the superagonistic mAbs, the so-called Fc portion. This dependence from Fc receptors is problematic, inter alia, because of the variable portion of Fc receptor-positive cells in preparations of peripheral blood cells and because of the variability of the antibody binding capacity caused by different Fc receptor alleles. Furthermore, the repeated addition of Fc receptor-expressing non-T lymphocytes is necessary for a repeated in vitro stimulation of T lymphocytes by soluble superagonistic mAbs. For use with human beings, this requires additional logistic and safety measures.

It is well known to multiply T cells in a culture by using small beads to which are bound CD28-specific costimulatory mAbs as well as TCR (CD3)-specific mAbs. Here there is a first drawback that two different substances are required. This requires a considerable effort when preparing under GMP conditions, which are legally required for preparations intended for therapy. Further, it is disadvantageous that each of these substances needs to be used in a relatively high concentration, since due to the common immobilization not all the molecules are available on a bead for the necessarily simultaneous binding of target cells, not for steric reasons alone.

TECHNICAL OBJECT OF THE INVENTION

It is therefore the technical object of the invention to provide means, by which blood cells can be stimulated, and wherein the amount of required mAbs is lower than when using the same mAbs in a solution, which makes the stimulation independent from the presence or the quality of non-T cells carrying Fc-receptors, and which can be prepared in an easier way under GMP conditions.

BRIEF DESCRIPTION OF THE FIGURES

FIGS. 5a-5e shows the comparison of the stimulation of regular T-cell resulting; as a result not only CD25-T cells, but in particular also CD25+ T cells can be stimulated with the microparticles according to the invention

BASICS OF THE INVENTION AND EMBODIMENTS THEREOF

Figure 1:
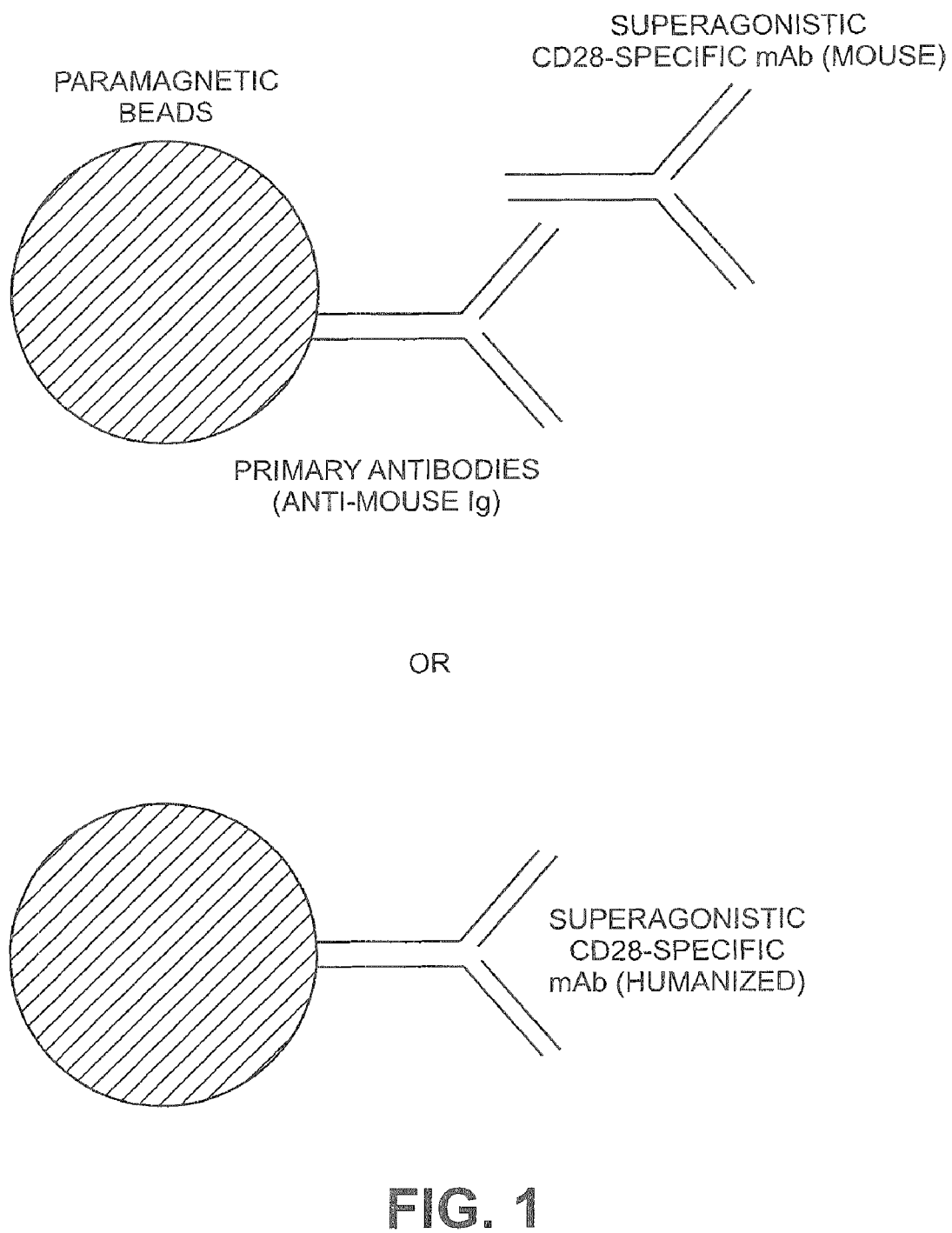
FIG. 1 shows that immunoglobulin binds the used mAb in a non-covalent manner.

For achieving this technical object, the invention teaches microparticles with a support structure and CD28-specific superagonistic monoclonal antibodies (mAbs) bonded to the support structure or a compound mimicking the above. Surprisingly, a lower amount of mAbs is required for a defined stimulatory effect by means of such immobilised mAbs, or with the same amount, a stronger stimulatory effect is obtained. This is further achieved without needing a TCR signal. The bonding of TCR-specific antibodies or other costimulatory components to the support structure is not necessary, thus steric problems of a costimulation by immobilised substances being also avoided. For an in vitro stimulation of T cells, only two components are required in the cell culture (beside the medium), the T cells and the microparticles according to the invention. There is no need of "feeder" cells or coatings of plastic surfaces with antibody preparations crosslinking the mAbs.

In this context, another advantage has a special importance, namely that for the preparation of microparticles according to the invention, one antibody only is required, which substantially simplifies the preparation under GMP conditions.

In detail, the bonding of the mAbs to the support structure can be achieved in the most various ways. For instance it is possible that the mAbs are bonded directly and by electrostatic forces, van der Waals forces, hydrophobic interactions, preferably however covalently, to the surface of the support structure. The mAbs may however also be bonded indirectly to the surface of the support structure by a spacer compound preferably covalently connected with the surface of the support structure.

Spacer compounds may in principle be all organic molecules, which on the one hand comprise a group being reactive with reactive groups of the surface of the support structure and on the other hand are capable to bond mAbs. The bonding may take place by electrostatic forces, van der Waals forces, hydrophobic interactions or covalently. The spacer compound may in particular be selected from the group consisting of "organic polymers, peptides, proteins, immunoglobulins, and combinations of such substances". The spacer compound should be physiologically well tolerated.

With regard to the support structure, the composition thereof is uncritical, as long as a bonding of the mAbs or of a spacer compound can be established on the surface. It is clear that the materials of the support structure, at least as far as they can come into contact with cells or a solution, should be physiologically well tolerated. Suitably, the surface of the support structure is formed by an organic polymer, which is preferably selected from the group consisting of "polystyrene, polyurethane, polyester, polyvinylpyridine, polyvinylamine, polyethyleneimine, chitosan, and mixtures of such polymers". The organic polymer may comprise, for the purpose of the covalent bonding of mAbs or spacer compounds, reactive groups, which preferably is glycidylether. In case of the glycidylether group, a covalent bonding of a protein or peptide takes place by reaction of primary amine groups of the protein or peptide with this group.

Depending on the polymer used, it may be recommendable that the organic polymer is surface activated by treatment with an activation reagent, which preferably is p-toluenesulfonyl chloride.

The diameter of the support structure is suitably in the range from 0.1 μm to 100 μm, preferably in the range from 1 μm to 20 μm, in particular in the range from 1 μm to 10 μm. The particle size may for instance be determined by means of the laser diffractometry (Mastersizer x, Malvern Instruments, Herrsching) or the photon correlation spectroscopy (Zetasizer 4, Malvern Instruments, Herrsching). The surface of the support structure may be 1 to 10, preferably 1 to 4 times the geometric surface, assumed as a smooth sphere surface.

Suitable support structures are for instance magnetic beads, as are used for the cell separation by means of magnets, for instance Dynabeads supplied by Dynal, or also $SiO_2$ particles. Further it is possible to use support structures, which are preferably biologically decomposable, and thus the microparticles can without concerns be administered to a patient. Suitable polymers for such support structures are for instance described in the documents WO 01/05875, Kissel et al., Advanced Drug Delivery Reviews 54: 99-134 (2002). In the first document, there are basically involved polyethyleneimines (PEI) and derivatives thereof. Biologically decomposable polymers may also be charge-modified polyesters, polyvinylpyridines or polyvinylamines.

The invention further teaches the use of microparticles according to the invention for the stimulation of blood cells, in particular T lymphocytes, B lymphocytes, granulocytes, monocytes and/or thrombocytes. The stimulation may take place in vitro or in vivo (the latter in particular in the case of the CD28-negative cells). In the case of the T lymphocytes, at least several sub-groups are stimulated. Therefore, the use for preparing a pharmaceutical composition for the treatment of diseases with reduced blood cell counts, in particular reduced T lymphocyte counts, of immunopathologic diseases (examples see below) or for strengthening the immune reaction in case of vaccinations is included, wherein a blood sample is taken from a patient, wherein as an option the blood cells are isolated from the blood sample, wherein the blood cells are cultivated in vitro under addition of a physiologically effective dose of microparticles, and wherein the thus obtained blood cells are as an option galenically prepared for the injection or infusion. Equally included is the use of microparticles according to the invention for preparing a pharmaceutical composition for the treatment of diseases with reduced blood cell counts, of immunopathologic diseases (for instance rheumatoid arthritis, inflammatory intestinal diseases, diabetes requiring insulin treatment, multiple sclerosis or the Guillain-Barré syndrome) or for strengthening the immune reaction in case of vaccinations, wherein the microparticles are galenically prepared for the injection or infusion. The galenic preparation for the injection may be for the IM, IP or IV injection.

Finally, the invention relates to a method for preparing microparticles according to the invention, comprising the following steps: a) microparticles with a surface formed by one or several different organic polymers are prepared, b) as an option, the surface is activated, c) the thus obtained microparticles are incubated with a solution containing CD28-specific superagonistic mAbs, wherein the mAbs preferably are covalently bonded to the surface, or c') the thus obtained microparticles are first incubated with a solution containing a spacer compound, wherein the spacer compound preferably is covalently bonded to the surface, as an option followed by a washing step, and subsequently the microparticles with the bonded spacer compound are incubated with a solution containing CD28-specific superagonistic mAbs, wherein the mAbs are covalently or non-covalently bonded to the spacer compound, and e) the thus obtained microparticles carrying CD28-specific superagonistic mAbs are separated from the solution and as an option subjected to a washing step.

Finally, the invention relates to methods for the prophylaxis and/or treatment of the described diseases, wherein either the microparticles according to the invention, galenically suitably prepared, are administered to a patient, or wherein preferably autologous cells are stimulated in vitro by means of microparticles according to the invention, and are implanted after the stimulation without or with the microparticles, galenically suitably prepared.

Explanations about the microparticles apply in an analogous manner to the uses and methods according to the invention.

DEFINITIONS

The amino acid sequence of human CD28 is known under the accession No. NM__006139.

Superagonistic CD28-specific mAbs can for instance be obtained from hybridoma cells, as filed under the filing numbers DSM ACC2530 and DSM ACC2531. Humanised mAbs according to DSM ACC2530 comprise sequences of the light chain and of the heavy chain according to SEQ.-ID 1 and 2.

Stimulation or activation of blood cells, in particular T lymphocytes, is the increase of metabolic activity, enlargement of the cell volume, synthesis of immunologically important molecules, and initiation of the cell division (proliferation) upon an external stimulus.

Several sub-groups of the T cells means at least the sub-groups of the CD4 and CD8 T cells. To the CD4 T cells belong, beside the "normal" CD25-negative T cells, also the $CD4^+CD25^+$ cells, which are also known as regulatory T cells. After results in animal models, the present state of the art assumes that the latter play a role for numerous autoimmune and inflammatory diseases, such as multiple sclerosis, Guillain-Barré syndrome, demyelinating polyneuropathy etc. A useful marker for regulatory T cells is the strong expression of CTLA-4 (CD152), which is expressed by non-regulatory T cells only after activation and then only to a small extent.

The term mAbs comprises, in addition to structures of the conventional Fab/Fc type, also structures exclusively consisting of the Fab fragment. It is also possible to use the variable region only, the fragment of the heavy chains being connected with the fragment of the light chain in a suitable manner, for instance also by means of synthetic bridge molecules, such that the binding regions of the chains form the antibody binding site. The term antibodies also comprises (complete) chimeric and humanised antibodies.

The term mAbs further comprises peptides or proteins analogous to the mAbs. An analogous peptide or protein is a peptide or protein, the amino acid sequence of which differs from the one of the peptide or protein, to which it is analogous, binds however a defined binding partner of the mAb with at least identical affinity. Differences in the sequences may be deletions, substitutions, insertions and elongations. An analogous peptide or protein will usually have a tertiary (partial) structure being very similar to the peptide or protein and/or exposition of a (cell surface) protein and otherwise needs to have or to generate in the region analogous to the immediate binding region only of the peptide or protein a binding site for the defined binding partner.

A mimicking compound of an mAb is a natural or synthetic chemical structure behaving in a defined binding assay as a defined mAb mimicked by the mimicking compound.

Superagonistic modulation of the proliferation of blood cells, in particular T cells means that no costimulation, i.e. no further binding event in addition to an (initial) binding of an mAb or of a mimicking compound to CD28 is necessary for the stimulation or inhibition of the proliferation.

The term treatment also comprises the term prophylaxis.

In the following, the invention will be explained in more detail with reference to embodiments representing examples of execution only.

Example 1

Direct Coupling of mAbs to Magnetic Beads

Surface-activated magnetic beads supplied by Dynal (Dynabeads) are used. The surface of the beads is hydrophobic and carries glycidylether groups. A covalent binding of antibodies takes place by a reaction of primary amine groups of the antibodies with the glycidylether groups. The beads are uniformly shaped, superparamagnetic spheres with a core of $\gamma Fe_2O_3$ and $Fe_3O_4$, which is coated with a polystyrene envelope. The average diameter is 4.5 µm. The density is approx. 1.5 g/cm$^3$. The surface area is 1 to 4 m$^2$/g beads. The geometric surface area is $6\times10^{-4}$ m$^2$/$10^7$ Dynabeads (approx. 0.9 m$^2$/g). The magnetic properties are not relevant for the invention, assist however in handling during a preparation.

The desired number of beads is taken from the obtained suspension after thorough mixing of the suspension (Vortex, 5 min). The vessel with the beads is placed in a magnetic holder (30-60 s), thus the beads being pelletised. The supernatant is removed, and coupling buffer, in which the binding of the antibodies to the beads is to take place (0.1 M $H_3BO_4$, pH 8.5, adjusted with NaOH), is added. The beads are thoroughly resuspended (Vortex, at least 2 min) and washed in this way. This washing step is performed three times altogether.

For the coupling of the antibody, the beads are thoroughly resuspended (Vortex, 30-60 s) in fresh coupling buffer together with the CD28-specific superagonistic antibody (huIgG-5.11, fully humanised mAb of the IgG4 isotype, genetically derived from an mAb of DSM ACC2530). The concentration of the beads is $4\times10^8$/ml. Per $10^7$ beads each 5 µg purified mAb are used. The incubation vessel with the mixture is fixed at a rotator, by slow rotation of the incubation vessel the sedimentation of the beads and thus a separation of the reaction mixture is avoided. The incubation takes place for 20-24 h between 4° C. and 37° C., for instance 20° C.

After the incubation, the beads are pelletised by means of the magnetic holder, the supernatant is removed and stored for a protein content measurement. The beads are resuspended in washing buffer (PBS without $Ca^{2+}$ and $Mg^{2+}$, 0.1% BSA). The suspension is washed for 5 min at 4° C. on the rotator with slow rotation. This washing step is performed altogether three times with fresh washing buffer each time. After termination of the washing steps, the beads are resuspended in washing buffer and are ready to use. Storage takes place at 4° C.

A measurement of the protein content of the supernatant from the coupling results in a fraction of approx. 50% of the employed amount such that at most 50% of the employed amount can be assumed as coupled. Therefrom can be calculated a minimum number of beads of $4\times10^6$/µg coupled mAbs, or 2.5 µg mAbs/$10^7$ beads.

Example 2

Indirect Coupling of mAbs to Magnetic Beads

In principle, an analogous approach to Example 1 is followed, with the only exception that anti-mouse Ig Dynabeads are used. These are beads, at the surface of which sheep anti-mouse immunoglobulin is covalently coupled. As a coupling buffer, a phosphate-buffered physiological common salt solution (PBS) is used. As mAbs were employed mouse anti-human CD28-specific superagonistic mAbs, which can be obtained from DSM ACC2530. The specificity fully corresponds to that of the mAbs used in Example 1, since agreement exists in the antigen binding regions. To the immunoglobulin binds the used mAb in a non-covalent manner according to FIG. 1.

Example 3

In Vitro Stimulation in a PBMC System

Figure 2:
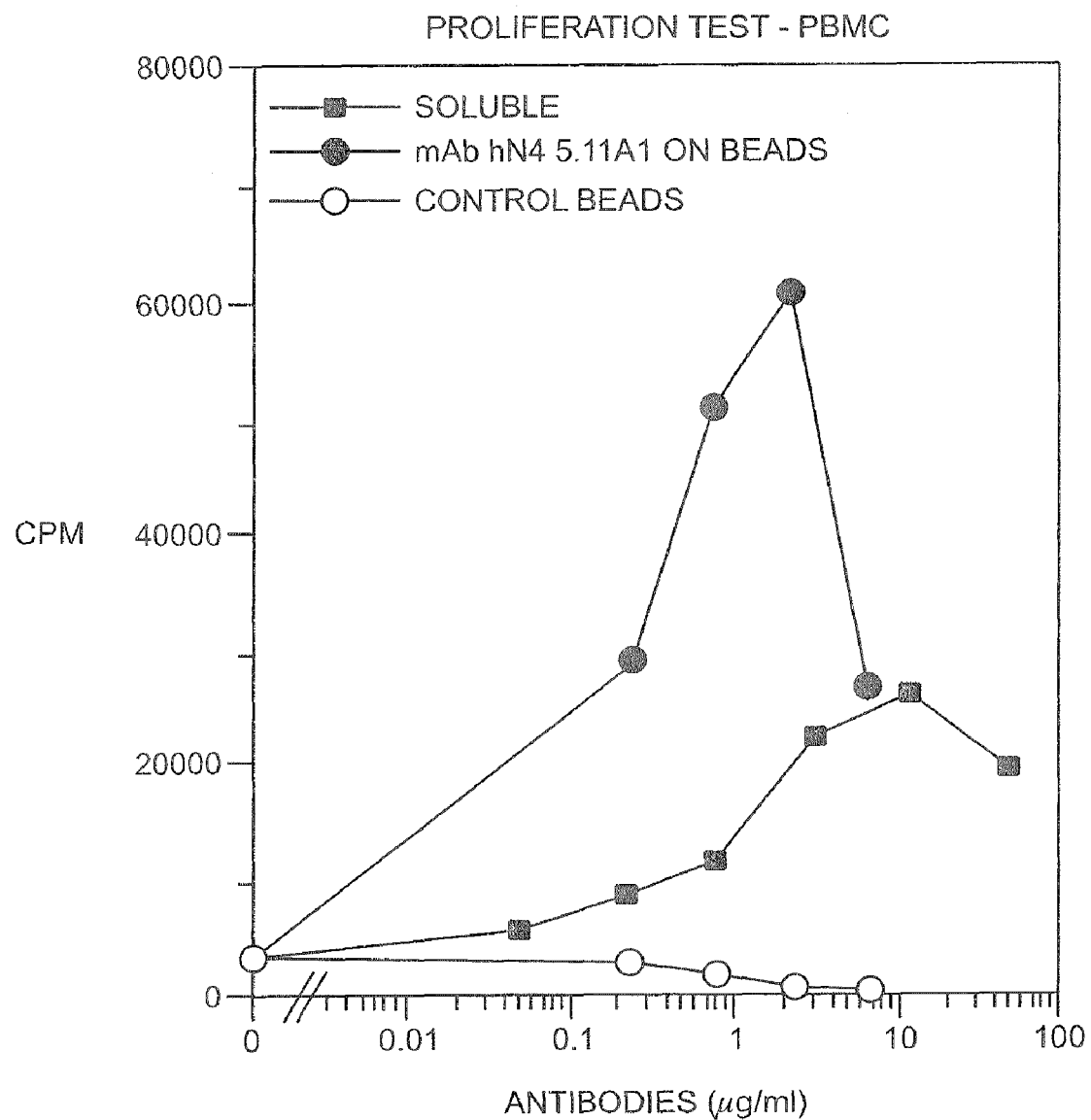
FIG. 2 shows a comparison of the capability of the humanised superagonistic mAb hN4 5.11A1 to stimulate unseparated human pBMCs in a soluble form to that of a bead-coupled form.

Per well of a 96-well plate were cultivated $2\times10^5$ PBMCs (peripheral blood mononuclear cells, i.e. T lymphocytes, B lymphocytes and monocytes) in 0.2 ml RPMI 1640 culture medium with 10% autologous serum. From day 2 to day 3, a 16-hour pulse was performed with 1 µCi $^3H$ thymidine, whereupon the thymidine incorporated into the DNA was measured as a proof for the proliferation. The results of FIG. 2 compare the capability of the humanised superagonistic mAb hN4 5.11A1 to stimulate unseparated human pBMCs (i.e. a mixture of T lymphocytes and Fc receptor-supporting non-T lymphocytes) in a soluble form compared to a bead-coupled form. On the abscissa, the antibody amount in fact introduced into the system (in a soluble form or bound to beads) is shown. The ordinate shows the incorporated radioactivity as a measure for the proliferation. This representative experiment clearly indicates that firstly the antibody coupled to beads induces in an optimum case a by far stronger proliferation than the one added in a soluble form only, and that secondly the specific activity of the antibody in the meaning of the proliferation induction is approx. 10 times higher when bound to beads than when adding the isolated antibody.

Example 4

In Vitro Stimulation of Isolated T Lymphocytes

Figure 3:
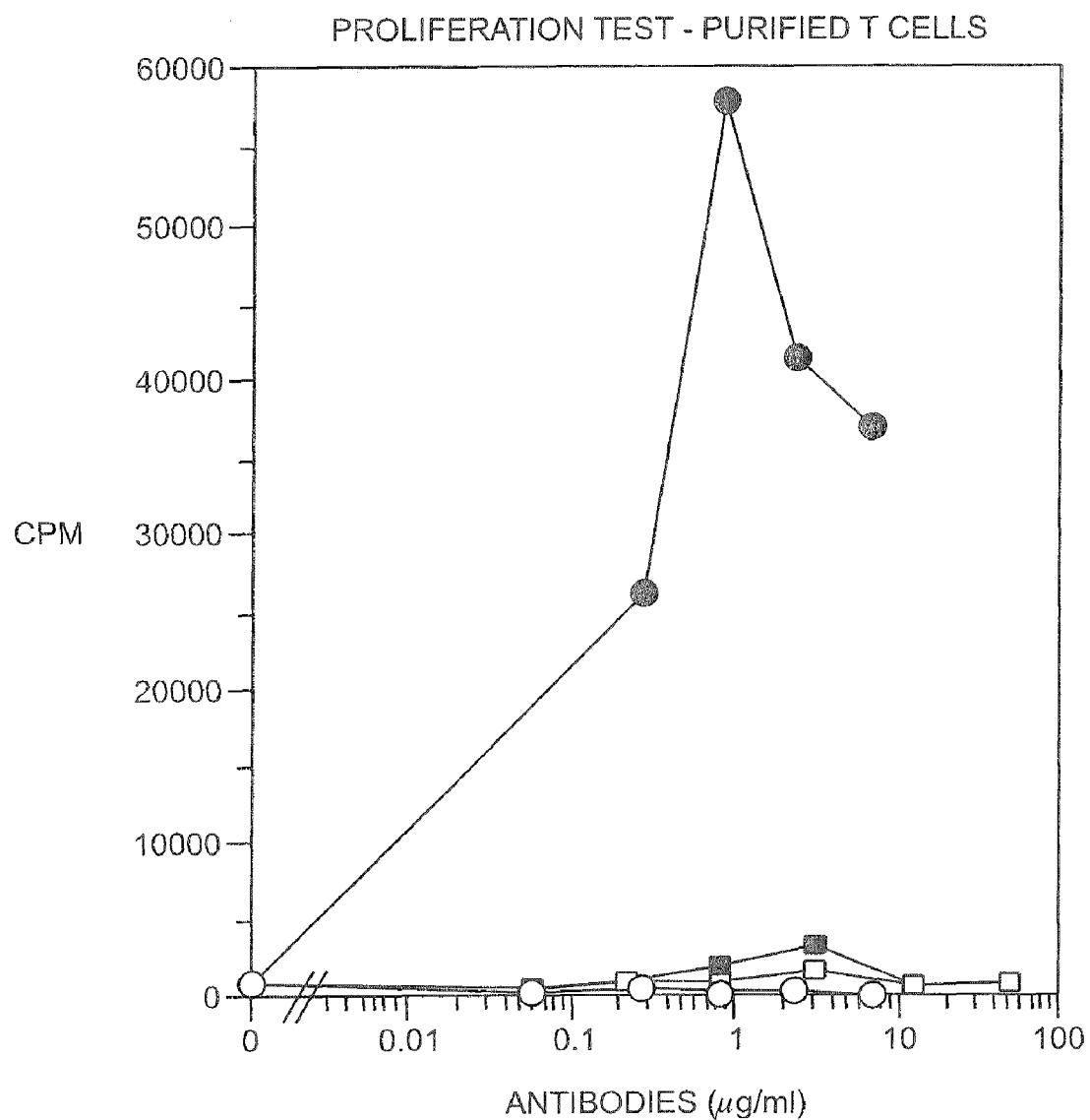
FIG. 3 shows a comparison of microparticles from Example 1 that of microparticles used in Example 1 not coupled with mAbs.

Under otherwise identical cultivation and measurement conditions as in Example 3, $2\times10^5$ purified T lymphocytes per well were used (obtained by means of nylon wool filtration). In FIG. 3 is shown a comparison when using microparticles from Example 1 to when using the microparticles used in Example 1, however not coupled with mAbs. In addition, the stimulating effect with solubly added mAbs in presence and absence of a secondary antibody (donkey anti-human Ig) coupled to the plastic surface is compared. It can be seen that unconjugated microparticles do not cause a proliferation, whilst the microparticles carrying mAbs show a very strong activity. This is many times higher than the activity, which is achieved by soluble mAbs in presence or absence of the immobilised secondary antibody. The very low stimulation compared to unseparated PBMCs (FIG. 2) by solubly added antibodies is expected, since cells with receptors for the Pc part of the antibody (FcR) are missing. The presence of the immobilised secondary reagent leads to a slight increase of the reactivity on solubly added antibodies. The beads accept the function of FC receptor-positive cells, however many times more efficient.

Example 5

Stimulatable T Cell Sub-Groups

Figure 4A:
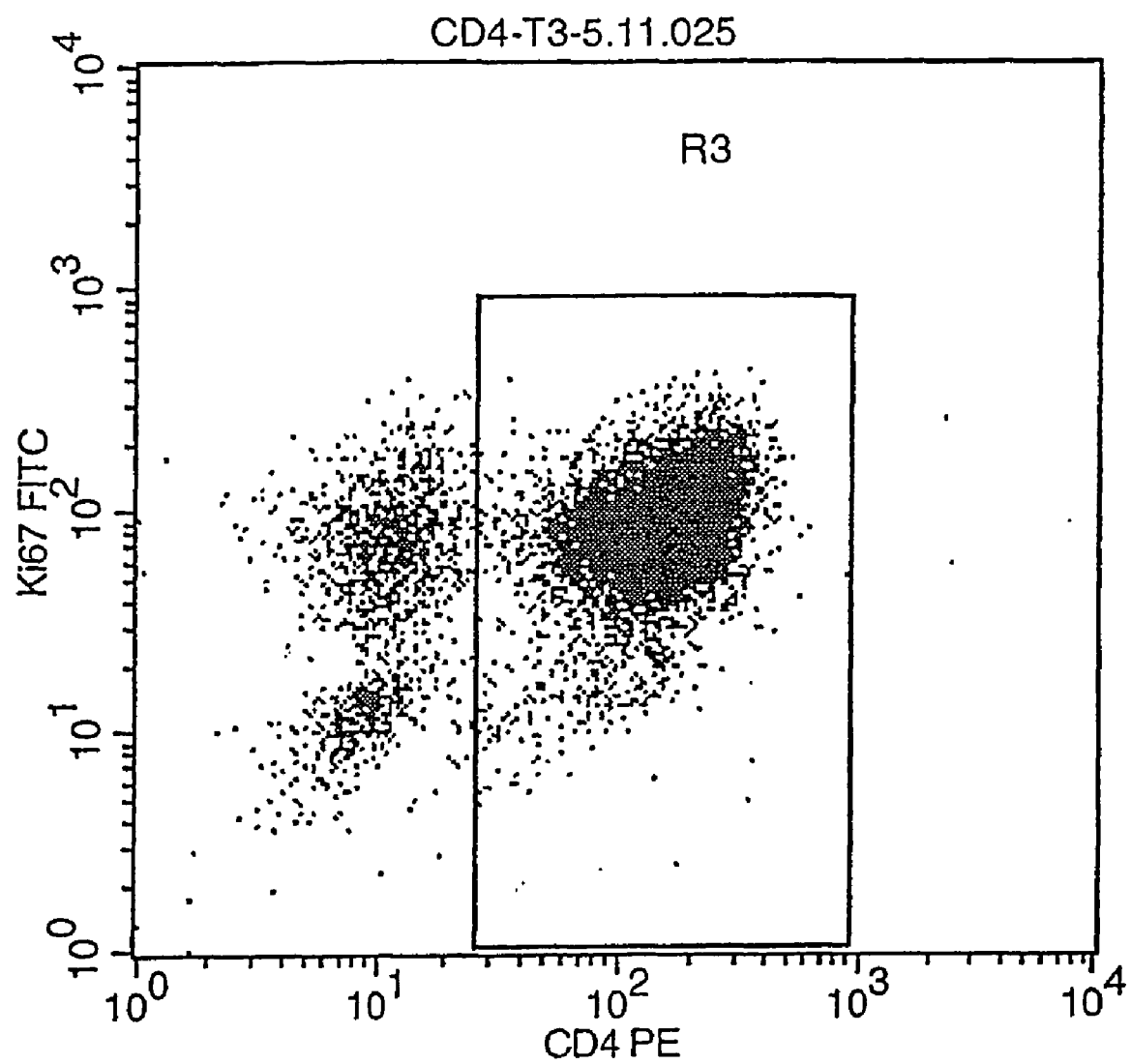
FIGS. 4a-4f shows the comparison of the stimulation of T-cell sub-groups with microparticles according to the invention, practically all CD4 T cells and the majority of the CD8 T cells are Ki67-positive and consequently proliferate.
Figure 4B:
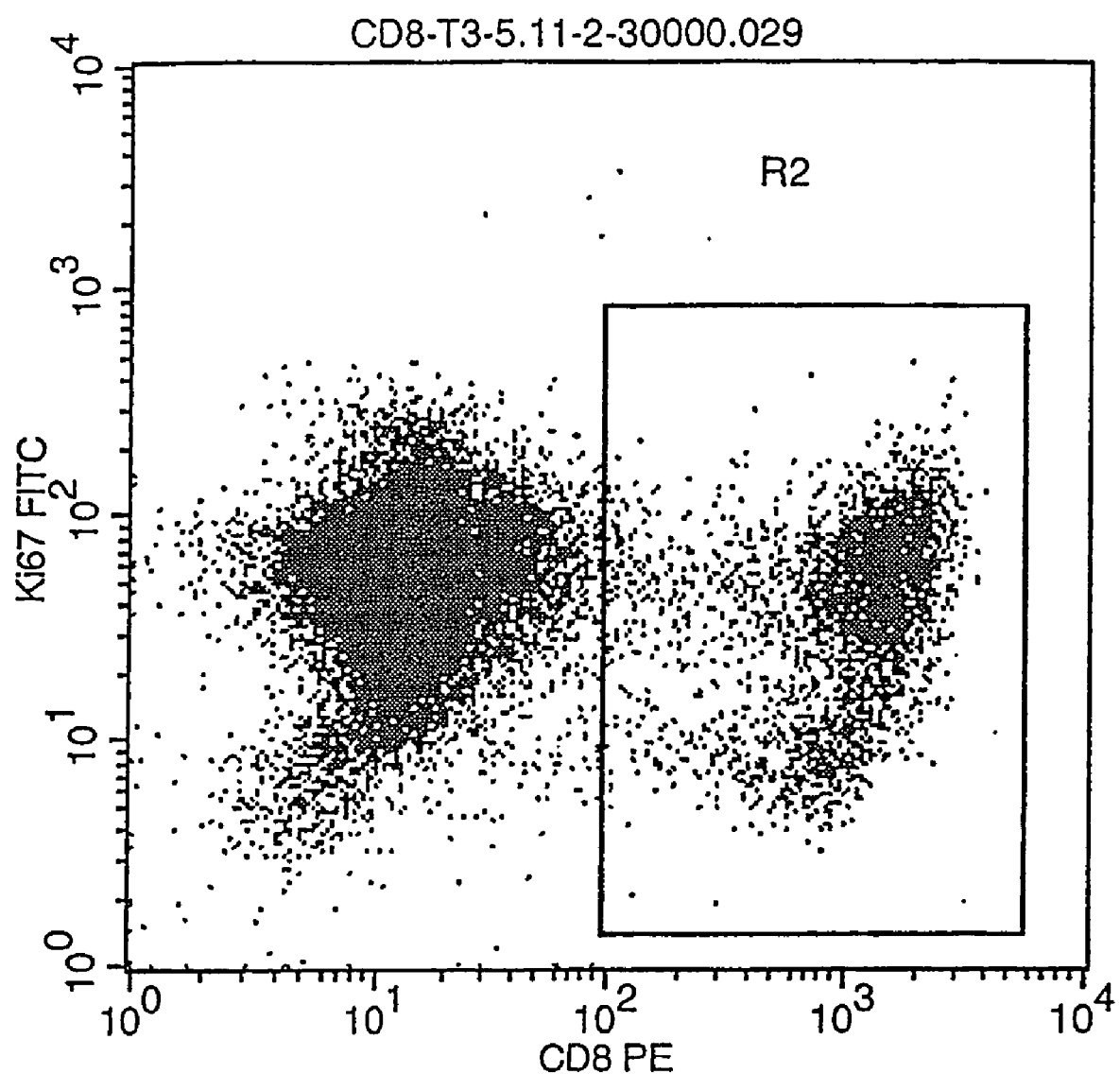
Figure 4C:
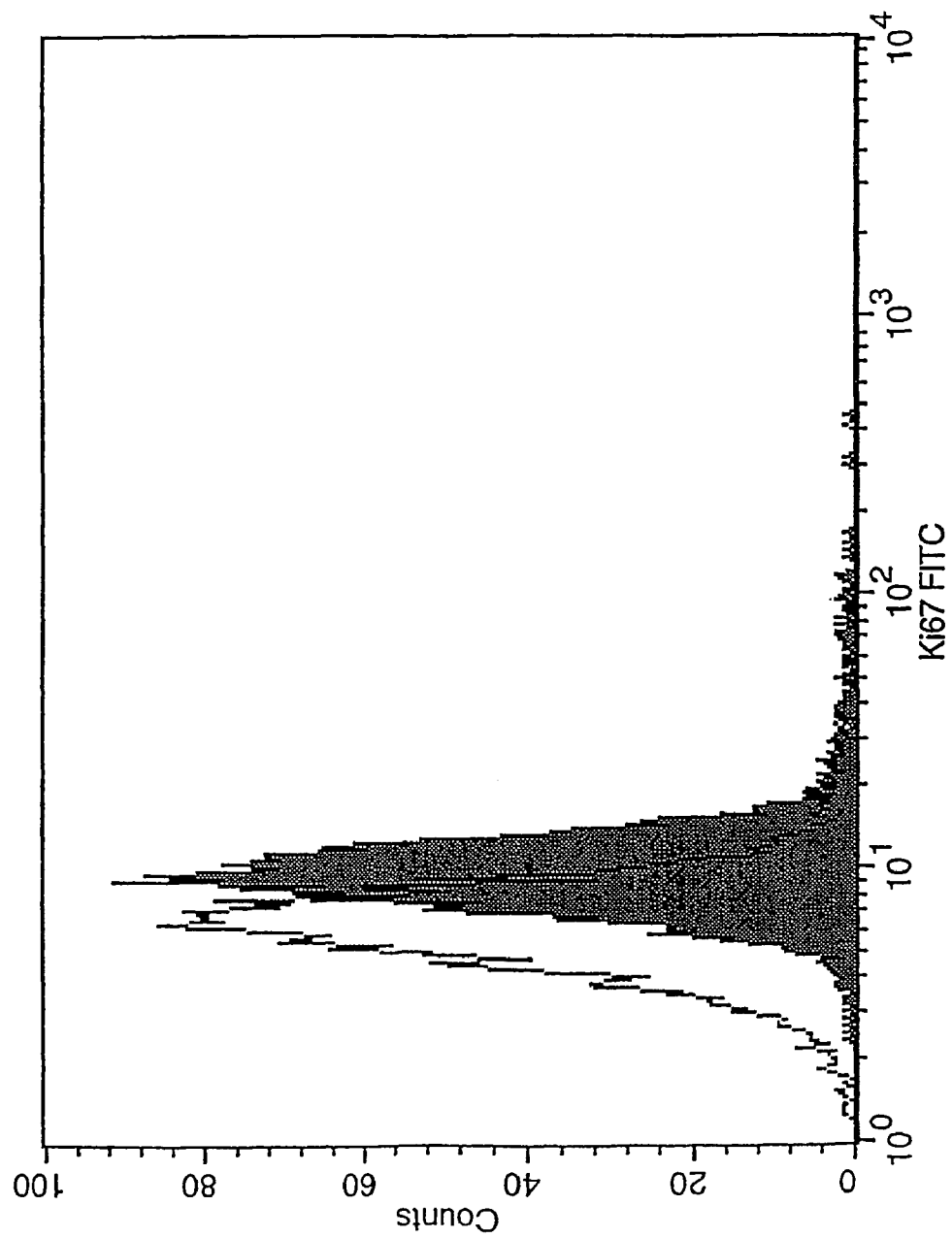
Figure 4D:
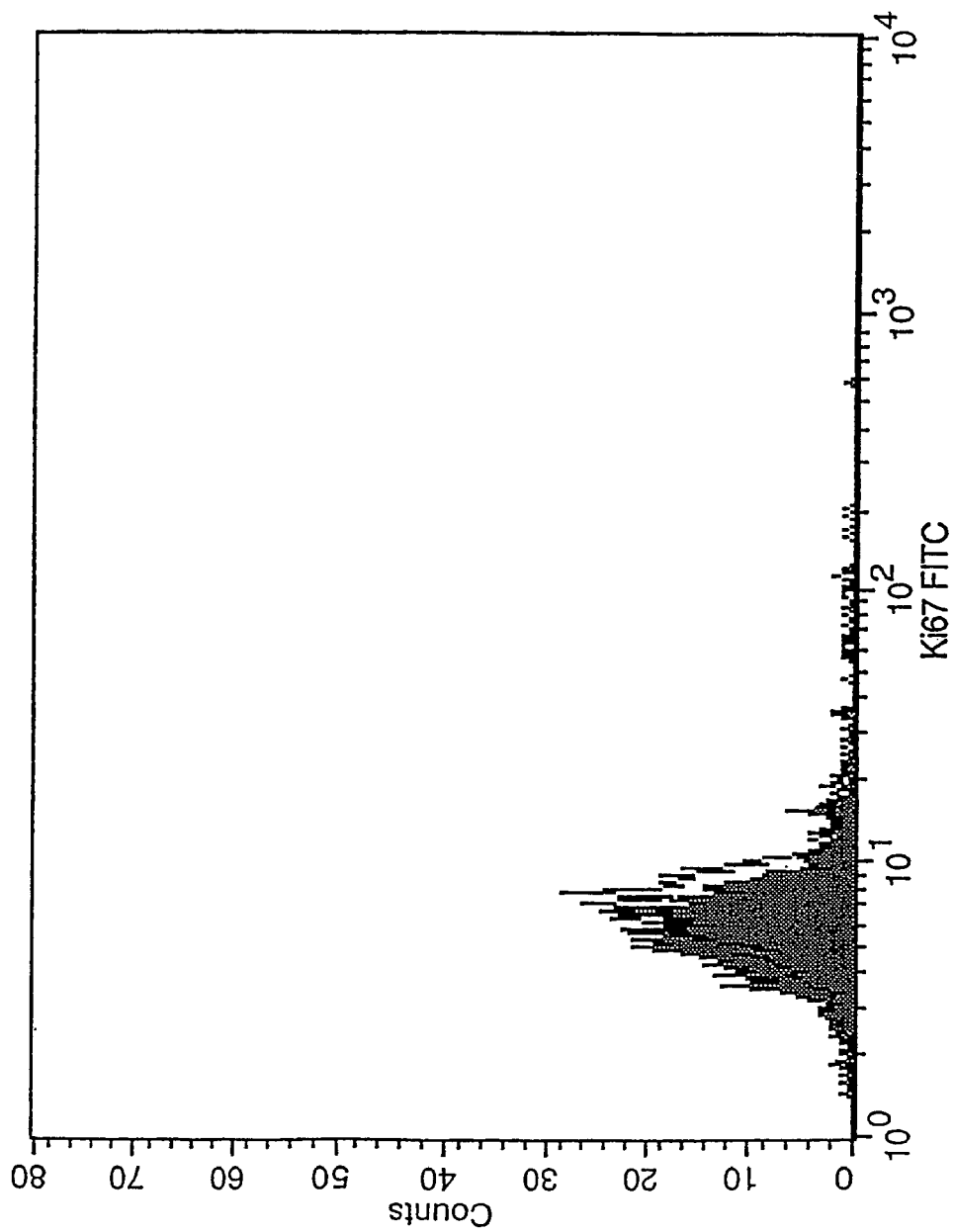
Figure 4E:
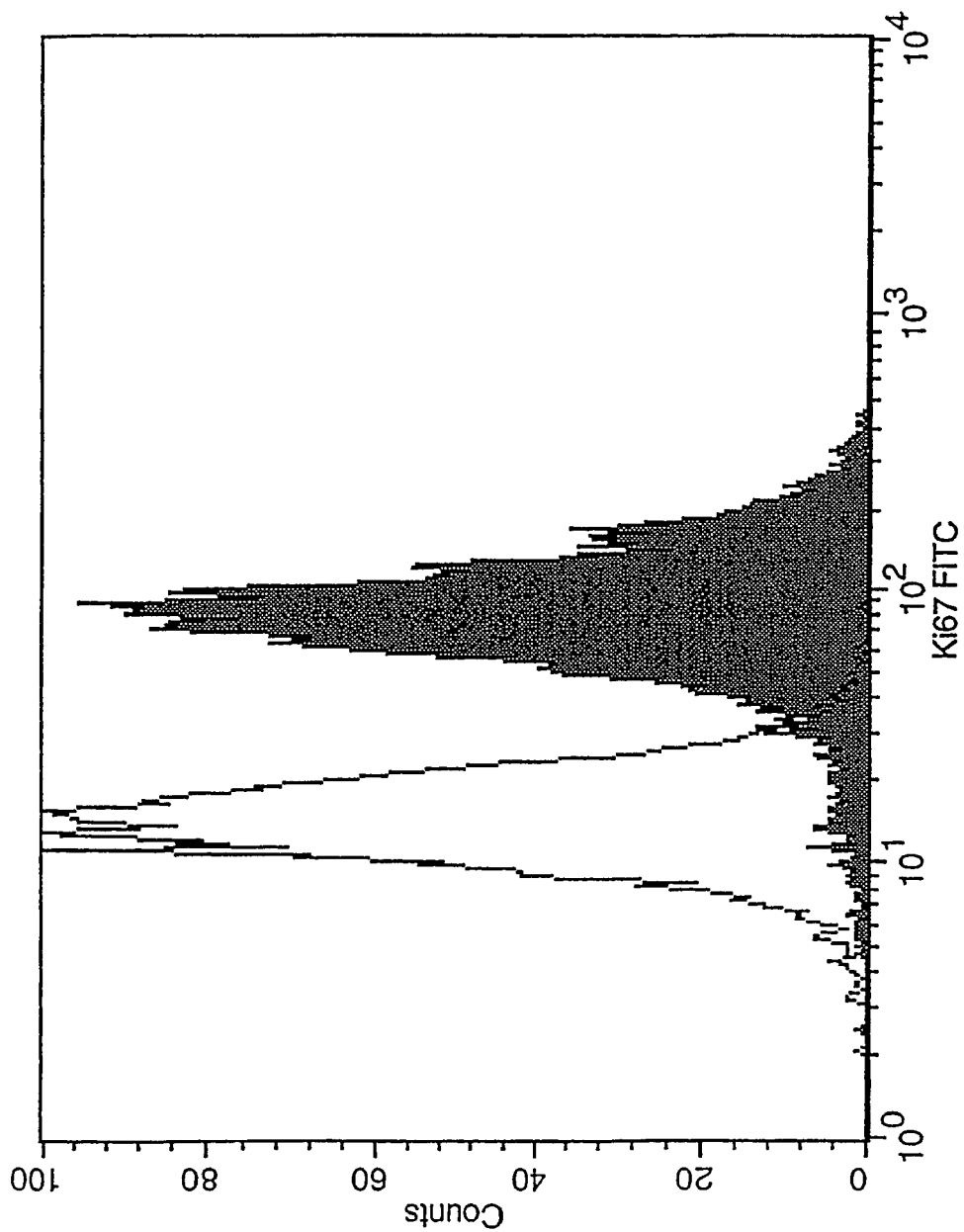
Figure 4F:
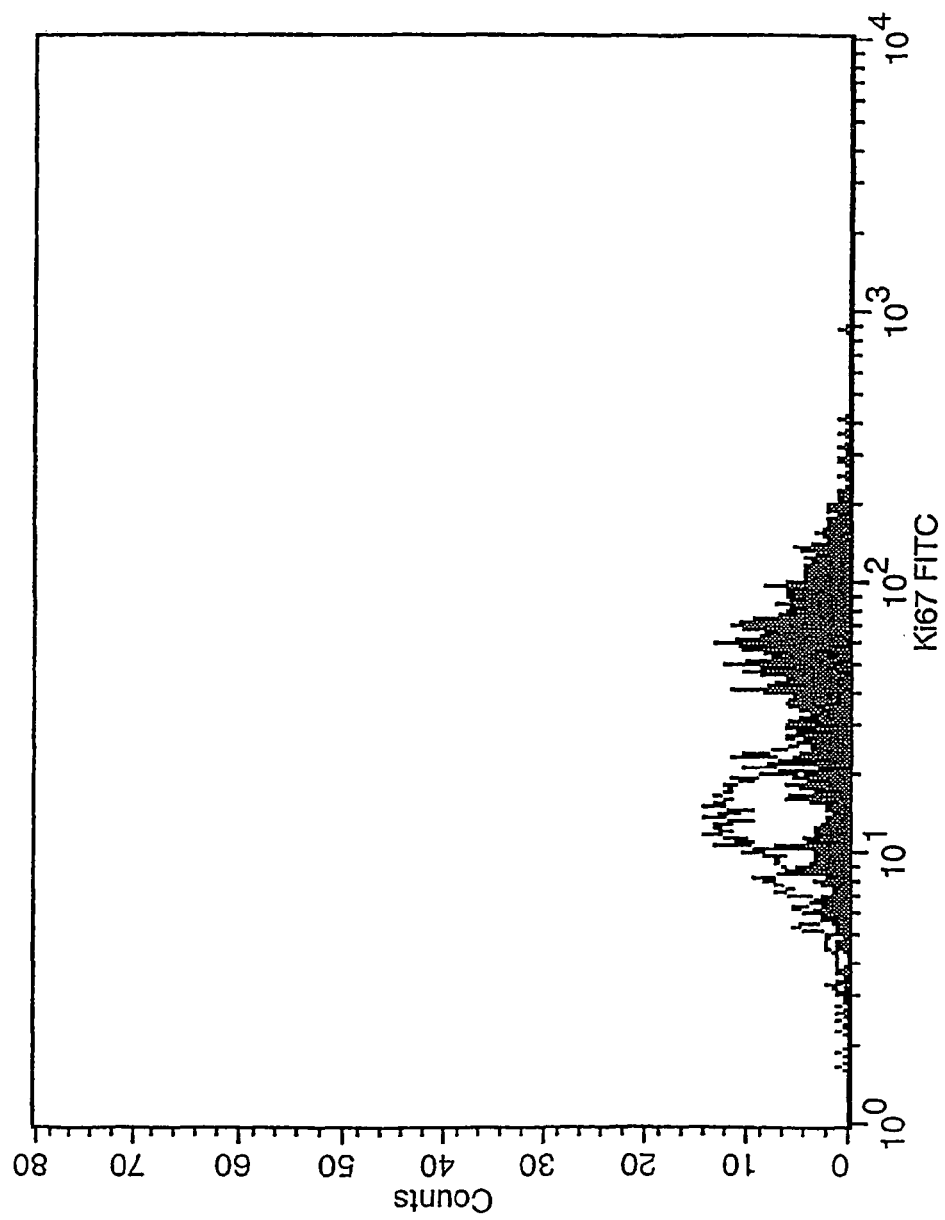

Purified T lymphocytes were cultivated according to Example 4, and microparticles according to Example 2 were used. After a 3-day culture, the cells were investigated in the FACS for the expression of the nuclear proliferation marker Ki67 after intracellular staining. The CD4 or CD28 T cells, resp., were selectively analysed by electronic gating after simultaneous staining with a CD4 or CD8-specific antibody. The used windows are shown in FIGS. 4a ($CD4^+$ cells) and 4b ($CD8^+$ cells). PE is the fluorescent dye phycoerythrin. In the histograms of FIGS. 4c to 4f only were entered the cells from the section respectively enclosed by boxes (FIGS. 4c and 4e: $CD4^+$ cells; FIGS. 4d and 4f: $CD8^+$ cells). In the histograms, a control staining with an irrelevant antibody (open curves) and the Ki67 staining was made. FITC is the fluorescent dye fluorescein isothiocynate. A comparative evaluation of FIGS. 4c and 4d on the one hand and of FIGS. 4e and 4f on the other hand shows that without stimulation, control and Ki67 histograms do not differ significantly. In contrast, with stimulation with the microparticles according to the invention, practically all CD4 T cells and the majority of the CD8 T cells are Ki67-positive and consequently proliferate. The histograms of FIGS. 4d and 4f are flatter than those of FIGS. 4c and 4e, since less CD8 than CD4 T cells are present.

Example 6

Stimulation of Regulatory T Cells

Figure 5A:
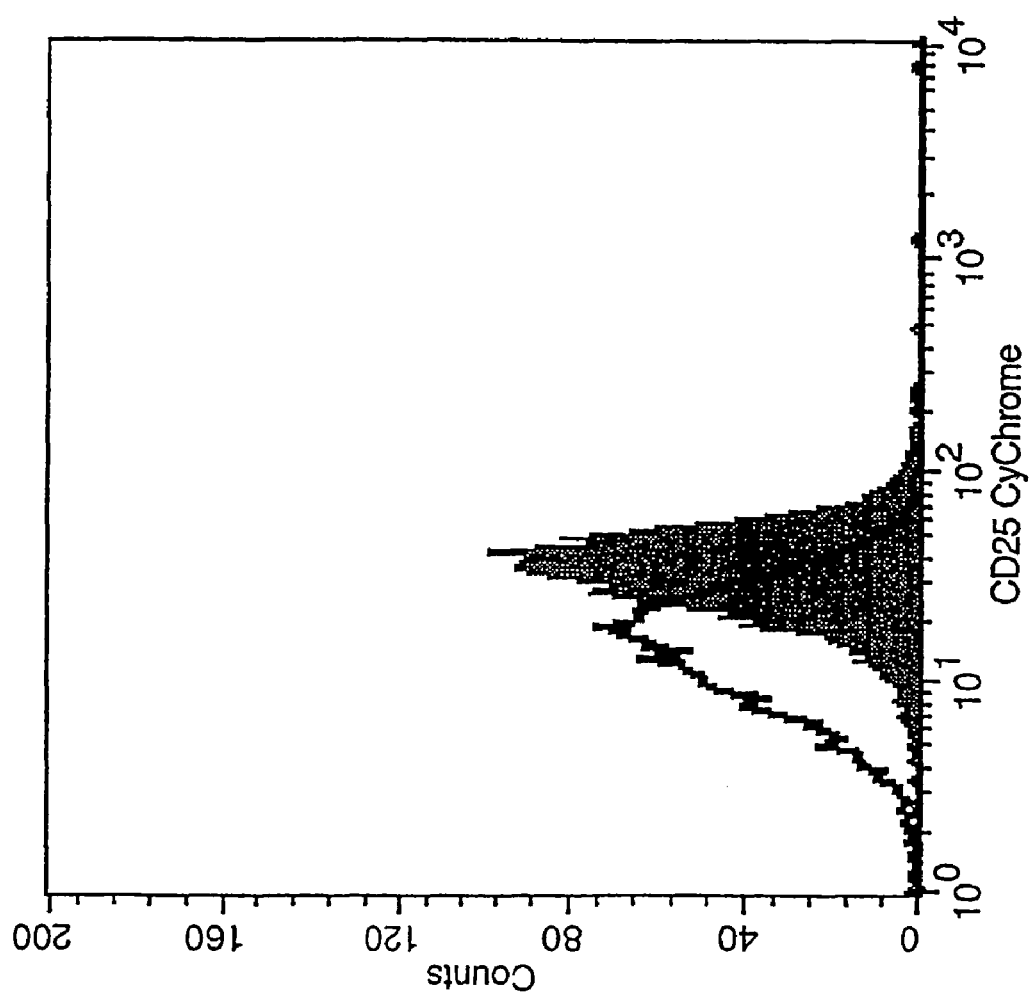

Human CD4 T cells were purified by nylon wool filtration and immune-magnetic depletion from all other PBMC populations. Thereupon the obtained CD4 T cells were separated into CD25-positive and CD25-negative fractions by means of magnetic cell sorting (system MACS, Miltenyi Biotech, Bergisch Gladbach, Germany). In FIG. 5a is shown the histogram form of the CD25 expression of the two purified populations of CD4 T cells. The CD25 expression is visible by the displacement toward the right of the filled distribution curve of the fluorescence (CyChrome-coupled CD25-specific mAbs) compared to the empty curve for CD25-negative cells.

Figure 5B:
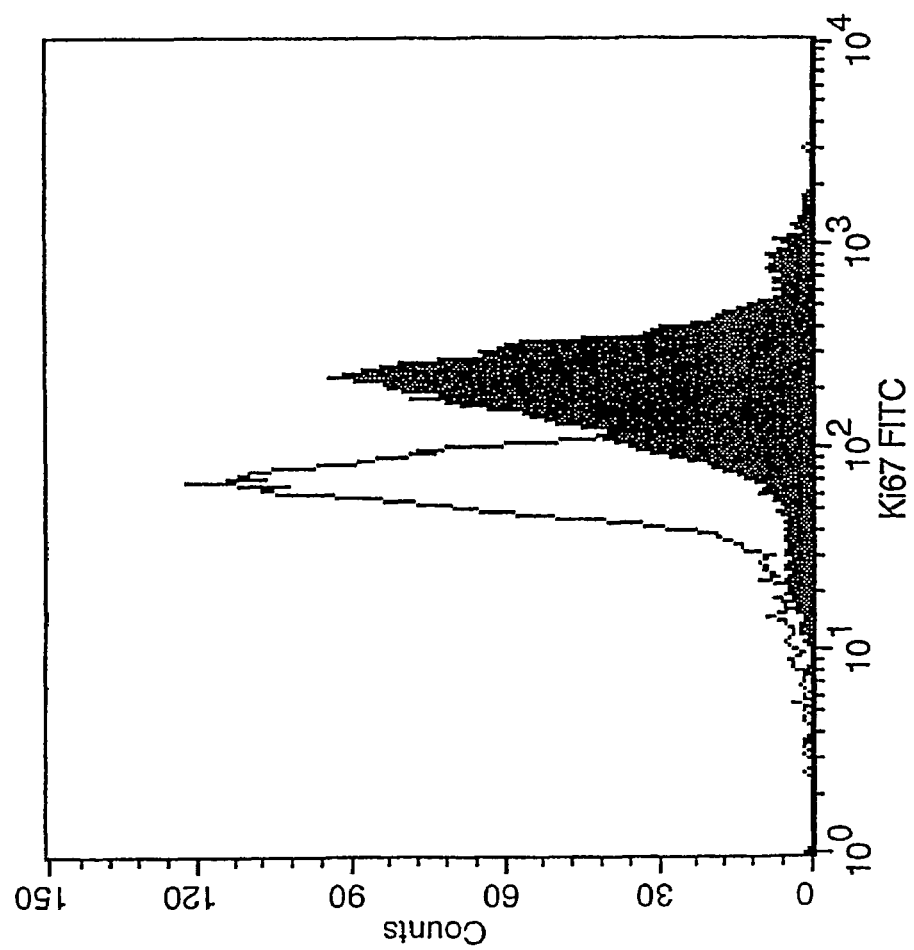
Figure 5C:
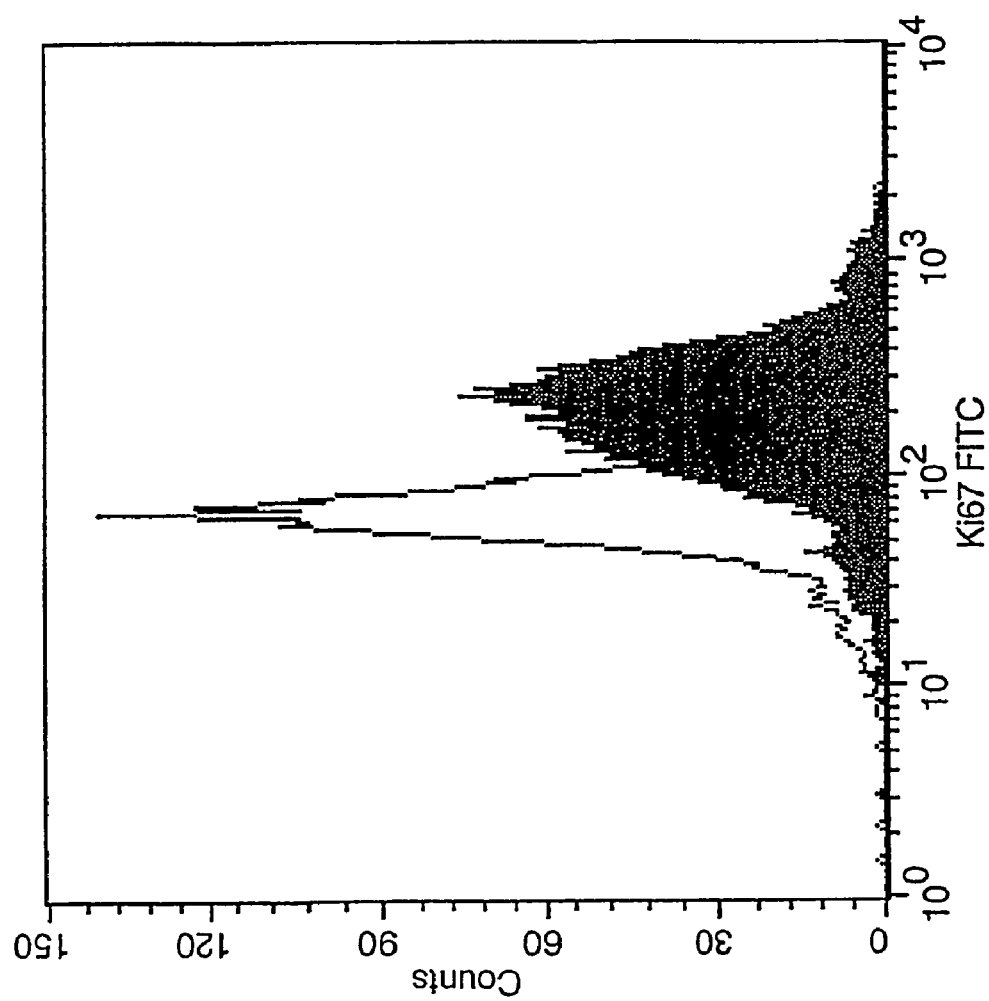
Figure 5D:
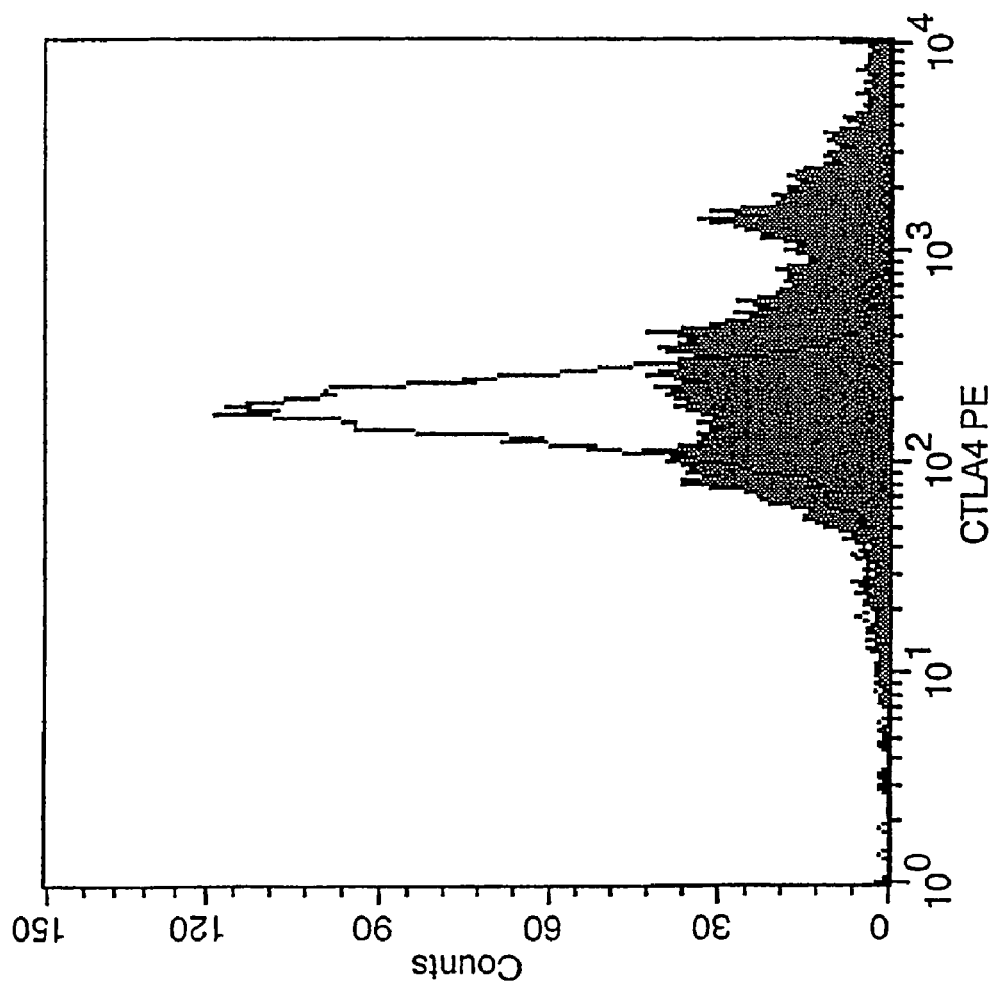

The CD4 T cells obtained as described above were stimulated for 3 days with microparticles according to Example 2. Then, by intracellular staining, the expression of Ki67 (proliferation) and CTLA-4 (strong expression indicates regulatory T cells) was analysed. FIGS. 5b and 5d show the results for CD25-negative T cells, and the open curves were again obtained with an irrelevant mAb for control purposes. FIG. 5b confirms that the $CD25^-$ cells proliferate. Only a small part of the $CD25^-$ cells express CTLA-4, as can be seen in FIG. 5d. FIG. 5c shows that the $CD25^+$ cells proliferate, too. FIG. 5e confirms that the majority of the $CD25^+$ cells strongly express CTLA-4. As a result, it is shown that not only $CD25^-$ T cells, but in particular also $CD25^+$ T cells can be stimulated with the microparticles according to the invention.

The invention claimed is:

1. A microparticle with a support structure and CD28-specific superagonistic monoclonal antibodies (mAbs) bonded to the support structure, wherein the surface of the support structure is formed by an organic polymer, which is selected from the group consisting of polystyrene, polyurethane, polyester, polyvinylpyridine, polyvinylamine, polyethyleneimine, chitosan, and mixtures of such polymers.

2. A microparticle according to claim 1, wherein the organic polymer comprises a reactive group that is glycidylether.

3. A microparticle according to claim 1, wherein the organic polymer is surface activated by treatment with an activation reagent, referred to as p-toluenesulfonyl chloride.

4. A microparticle according to claim 1, wherein the surface of the support structure (measured by means of the BET method) is 1 to 10 times the geometric surface, assumed as a smooth sphere surface.

5. A microparticle according to claim 1, wherein the surface of the support structure (measured by means of the BET method) is 1 to 4 times the geometric surface, assumed as a smooth sphere surface.

* * * * *